United States Patent
McDonald et al.

(10) Patent No.: US 6,939,554 B2
(45) Date of Patent: *Sep. 6, 2005

(54) ANTIMICROBIAL POLYMER

(75) Inventors: William F. McDonald, Utica, OH (US); Zhi-Heng Huang, Walnut Creek, CA (US); Stacy C. Wright, Columbus, GA (US)

(73) Assignee: Michigan Biotechnology Institute, Lansing, MI (US)

( * ) Notice: Subject to any disclaimer, the term of this patent is extended or adjusted under 35 U.S.C. 154(b) by 104 days.

This patent is subject to a terminal disclaimer.

(21) Appl. No.: 10/068,054

(22) Filed: Feb. 5, 2002

(65) Prior Publication Data
US 2003/0157193 A1 Aug. 21, 2003

(51) Int. Cl.[7] .......................... A01N 25/00; A61K 31/74
(52) U.S. Cl. ................ 424/405; 424/78.08; 424/78.31; 514/772; 514/772.3
(58) Field of Search .............................. 424/405, 78.08, 424/78.18, 78.31, 78.35; 514/772; 528/332

(56) References Cited

U.S. PATENT DOCUMENTS

| | | |
|---|---|---|
| 3,695,921 A | 10/1972 | Shepherd et al. |
| 4,054,139 A | 10/1977 | Crossley |
| 4,128,633 A | 12/1978 | Lorenz et al. ................ 424/80 |
| 4,217,338 A | 8/1980 | Quash |
| 4,302,368 A | 11/1981 | Dudley et al. |
| 4,310,509 A | 1/1982 | Berglund et al. ............. 424/28 |
| 4,323,557 A | 4/1982 | Rosso et al. .................. 424/28 |
| 4,357,476 A | 11/1982 | Reinchr et al. ............. 564/509 |
| 4,419,444 A | 12/1983 | Quash |
| 4,442,133 A | 4/1984 | Greco et al. .................... 427/2 |
| 4,581,028 A | 4/1986 | Fox, Jr. et al. |
| 4,603,152 A | 7/1986 | Laurin et al. |

(Continued)

FOREIGN PATENT DOCUMENTS

| | | |
|---|---|---|
| EP | 0 882 461 | 12/1998 |
| EP | 0 969 056 | 1/2000 |
| GB | 2084466 | 4/1982 |
| GB | 2 153 235 | 8/1985 |
| GB | 2 225 580 | 6/1990 |
| JP | 59112070 A2 * | 6/1984 |
| JP | 405000912 A | 1/1993 |

(Continued)

OTHER PUBLICATIONS

Satoh et al., "Immobilization of Saccharides and Peptides on 96–Well Microtiter Plates with Methyl Vinyl ether–Maleic Anhydride Copolymer", Anal. Biochem., 260, 96–102, 1998.

(Continued)

*Primary Examiner*—Thurman K. Page
*Assistant Examiner*—Lakshmi Channavajjala
(74) *Attorney, Agent, or Firm*—Foley & Lardner LLP (57) ABSTRACT

A polymeric composition having antimicrobial properties and a process for rendering the surface of a substrate antimicrobial are disclosed. The composition comprises a crosslinked chemical combination of (i) a polymer having amino group-containing side chains along a backbone forming the polymer, (ii) an antimicrobial agent selected from quaternary ammonium compounds, gentian violet compounds, substituted or unsubstituted phenols, biguanide compounds, iodine compounds, and mixtures thereof, and (iii) a crosslinking agent containing functional groups capable of reacting with the amino groups. In one embodiment, the polymer is a polyamide formed from a maleic anhydride or maleic acid ester monomer and alkylamines thereby producing a polyamide having amino substituted alkyl chains on one side of the polyamide backbone; the crosslinking agent is a phosphine having the general formula $(A)_3P$ wherein A is hydroxyalkyl; and the antimicrobial agent is chlorhexidine, dimethylchlorophenol, cetyl pyridinium chloride, gentian violet, triclosan, thymol, iodine, and mixtures thereof.

51 Claims, 4 Drawing Sheets

U.S. PATENT DOCUMENTS

| | | | |
|---|---|---|---|
| 4,605,564 A | 8/1986 | Kulla et al. ..................... 427/2 | |
| 4,642,104 A | 2/1987 | Sakamoto et al. ........... 604/264 | |
| 4,675,347 A | 6/1987 | Mochizuki et al. .......... 523/122 | |
| 4,678,660 A | 7/1987 | McGary et al. ................ 424/25 | |
| 4,720,512 A | 1/1988 | Hu et al. | |
| 4,786,556 A | 11/1988 | Hu et al. | |
| 4,865,870 A | 9/1989 | Hu et al. | |
| 4,933,178 A | 6/1990 | Capelli | |
| 4,987,181 A | 1/1991 | Bichon et al. | |
| 4,999,210 A | 3/1991 | Solomon et al. ................ 427/2 | |
| 5,019,096 A | 5/1991 | Fox, Jr. et al. | |
| 5,019,102 A | 5/1991 | Hoene ......................... 623/12 | |
| 5,069,907 A | 12/1991 | Mixon et al. ................ 424/445 | |
| 5,135,811 A | * 8/1992 | White et al. ................. 428/395 | |
| 5,316,912 A | 5/1994 | Heimgartner et al. | |
| 5,328,698 A | * 7/1994 | Onwumere et al. ......... 424/486 | |
| 5,344,411 A | 9/1994 | Domb et al. | |
| 5,405,919 A | 4/1995 | Keefer et al. | |
| 5,641,855 A | 6/1997 | Scherr et al. | |
| 5,650,447 A | 7/1997 | Keefer et al. | |
| 5,707,366 A | 1/1998 | Solomon et al. ............ 604/265 | |
| 5,709,672 A | 1/1998 | Illner ......................... 604/265 | |
| 5,762,638 A | 6/1998 | Shikani et al. | |
| 5,962,520 A | 10/1999 | Smith et al. | |
| 6,030,632 A | 2/2000 | Sawan et al. | |
| 6,042,877 A | 3/2000 | Lyon et al. | |
| 6,056,967 A | 5/2000 | Steuerle et al. | |
| 6,087,462 A | 7/2000 | Bowers et al. | |
| 6,121,027 A | 9/2000 | Clapper et al. | |
| 6,153,724 A | 11/2000 | Hollingsworth ............. 528/310 | |
| 6,162,487 A | 12/2000 | Darouiche .................. 427/2.14 | |
| 6,224,579 B1 | 5/2001 | Modak et al. ............... 604/265 | |
| 6,232,336 B1 | 5/2001 | Hrabie et al. | |
| 6,232,434 B1 | 5/2001 | Stamler et al. | |
| 6,319,674 B1 | 11/2001 | Fulcrand et al. | |
| 6,340,465 B1 | 1/2002 | Hsu et al. | |
| 6,365,066 B1 | * 4/2002 | Podszun et al. ............. 252/380 | |
| 6,399,714 B1 | 6/2002 | Huang et al. | |
| 6,495,657 B1 | 12/2002 | McDonald et al. | |
| 6,509,104 B2 | 1/2003 | Huang et al. | |

FOREIGN PATENT DOCUMENTS

| | | |
|---|---|---|
| JP | 11 222 402 | 8/1999 |
| WO | WO 86/02561 | 5/1986 |
| WO | WO 94/13870 | 6/1994 |
| WO | WO 95/05400 | 2/1995 |
| WO | WO 00/17254 | 3/2000 |
| WO | WO 01/11956 | 2/2001 |

OTHER PUBLICATIONS

Vercruysse et al., "Synthesis and in Vitro Degradation of New Polyvalent Hydrazide Cross–Linked Hydrogels of Hyaluronic Acid", Bioconj. Chem., 8, 686–694, 1997.

O'Shannessy et al., Immobilization of Glycoconjugates by Their Oligosaccharides: Use of Hydrazido–Derivatized matrices, Anal. Biochem., 191, 1–8, 1990.

Ito et al., Preparation of High Capacity Affinity Adsorbents Using New Hydrazino–Carriers and Their Use for Low and High Performance Affinity Cheomatography of Lectins, J. Biochem. (Tokyo), 99, 1267–1272, 1986.

Junowicz et al., The Derivatization of Oxidized Polysaccharides for Protein Immobilization and Affinity Chromatography Biochim. Biophys. Acta 428, 157–165, 1976.

Miron et al., Polyacrylhyrdazio–Agarose: Preparation via Periodate Oxidation and use for Enzyme Immobilization and Affinity Chromatography, J. Chromatogr., 215, 55–63 1981.

Heimgartner, et al., Polyacrylic Polyhydrazides as Reagents for Detection of Glycoproteins, Anal. Biochem., 181, 182–189, 1989.

Fleminger et al., Oriented Immobilization of Peridate–Oxidized Monoclonal Antibodies on Amino and Hydrazide Derivatives of Eupergit C, Applied Biochem., 23, 123–137, 1990.

Del Rosso et al., Binding of the Basement–Membrane Glycoprotein Lamnin to Glycosaminoglycans, Biochem. J., 1999, 699–704, 1981.

Henderson et al., Immobilised Phosphines Incorporation the Chiral Bioploymers Chitosan and Chitin, J. Chem. Soc., Chem. Commun., 9, 1863–1864, 1994.

Petach et al., A New Coupling Reagnet for the Covalent Immobilisation of Enzymes, J. Chem. Soc., Chem. Commun., 17, 2181–2182, 1994.

Cochrane et al., Application of Tris(hydroxymethyl) Phophine as a Coupling Agent for Alcohol Dehydrogenase Immobilization, Enzyme Microbial Technol., 18, 373–378, 1996.

Inman et al., Synthesis of Large Haptenic Compounds Having a Covalent Functional Group That Permits Convalent Linkage to Proteins, Cell Surfaces, Immunochemistry, 10, 153–163, 1973.

Ellis et al., Water–Soluble Tris(hydroxymethyl) Phospine Complexes with Nickel, Palladium, and Platinum, Inorg. Chem., 31, 3026–3033, 1992.

Lin et al., Preparation of Surface–modified Albumin Nanospheres, Biomaterials, V. 18, N. 7, 559–565, 1997.

Marconi et al., New Polyurethane Compositions able to bond high Amounts of both Albumin and Heparin, V. 16, N. 6, 449–456, 1995.

Oswald et al., "Properties of a Thermostable B–Glycosides Immobilized Using Tris(hydroxymethyl) Phosphine as a Highly Effective Coupling Agent", Enzyme Microbial Technol., 23, 14–19, 1998.

Isosaki et al., Immobilization of Protein Ligands with methyl Vinyl Ether–maleic Anhydride Copolymer, J. Chromatogr., 597, 123–128, 1992.

Patent Abstracts of Japan vol. 1999, No. 13, (Nov. 30, 1999) & JP 11 222402 A (Osaka Gas Co. Ltd), (Aug. 17, 1999) abstract.

* cited by examiner

ANTIMICROBIAL POLYMER

STATEMENT REGARDING FEDERALLY SPONSORED RESEARCH OR DEVELOPMENT

This Invention was made with U.S. Government support under NREL Subcontract NO. XXE-9-29058-01, Prime Contract No. DE-AC36-98GO10337 awarded by the Department of Energy. The U.S. Government has certain rights in this invention.

BACKGROUND OF THE INVENTION

1. Field of the Invention

This invention relates to a polymeric composition having antimicrobial properties and a process for rendering the surface of a substrate antimicrobial. The polymeric composition is a crosslinked chemical combination of (i) a polymer having amino group-containing side chains along a backbone forming the polymer, (ii) an antimicrobial agent selected from quaternary ammonium compounds, gentian violet compounds, substituted or unsubstituted phenols, biguanide compounds, iodine compounds, and mixtures thereof, and (iii) a crosslinking agent containing functional groups capable of reacting with the amino groups on the polymer.

2. Description of the Related Art

Many medical procedures involve the placement of medical devices, such as catheters, endotracheal tubes, prostheses, grafts, sutures, dressings and implants, in the human body. Infection is a common complication associated with the use of such medical devices. Accordingly, many research efforts have concentrated on finding means to prevent infection associated with these implantable medical devices.

One solution to this infection problem has been the use of medical device coatings having antimicrobial agents. An "antimicrobial" agent is an agent that has antiviral, antibacterial, and/or antifungal properties. (Antiviral means capable of killing or suppressing the replication of viruses. Antibacterial means bacteriostatic or bactericidal where bactericidal means the killing of microorganisms and bacteriostatic means inhibiting the growth of microorganisms. Antifungal means capable of killing or suppressing replication of fungi.)

It has been particularly desirable to use a coating for implantable medical devices that is bacteriostatic, i.e., inhibits bacterial growth, such that the device can be implanted for longer periods without compromising the subject through a secondary bacterial infection. Various compounds have been incorporated into polymeric materials or polymeric coatings to provide for an implantable medical device that is bacteriostatic. For example, U.S. Pat. No. 6,224,579 B1 discloses polymeric medical articles comprising triclosan and/or other chlorinated phenols and silver containing compounds. U.S. Pat. Nos. 5,707,366, 4,999,210 and 4,675,347 disclose medical articles having a chlorhexidine coating. U.S. Pat. No. 5,709,672 discloses polymeric medical articles comprising gentian violet and/or silver containing compounds. U.S. Pat. No. 5,328,698 discloses polymeric medical articles comprising quaternary ammonium compounds. U.S. Pat. No. 5,069,907 discloses medical articles comprising triclosan. U.S. Pat. No. 6,162,487 discloses polymeric medical articles comprising chlorhexidine, methylisothiazolone, terpineol, thymol, chloroxylenol, and/or cetylpyridinium chloride. U.S. Pat. Nos. 4,323,557, 4,310,509 and 4,128,633 disclose medical articles having iodine compound coatings. U.S. Pat. No. 4,605,564 discloses polymeric medical articles comprising chlorinated phenols.

Even though various medical device coatings having antimicrobial agents are known, there is still a need for an improved antimicrobial polymer coating that may be easily applied to a substrate to provide an article which has excellent antimicrobial properties and which retains its antimicrobial properties in a permanent and non-leachable fashion when in contact with bodily fluids for prolonged periods. In addition, it would be beneficial if this coating could be combined with an anti-thrombogenic coating to prevent both clotting and bacterial infection.

SUMMARY OF THE INVENTION

The foregoing needs are met by a polymeric composition having antimicrobial properties, wherein the polymeric composition comprises a crosslinked chemical combination of (i) a polymer having side chains along a backbone forming the polymer, at least two of the side chains containing an amino group, (ii) an antimicrobial agent selected from quaternary ammonium compounds, gentian violet compounds, substituted or unsubstituted phenols, biguanide compounds, iodine compounds, and mixtures thereof, and (iii) a crosslinking agent containing at least two functional groups capable of reacting with the amino groups. An article according to the invention comprises a substrate and a coating of the polymeric composition disposed on at least a portion of the substrate.

The polymer used in the polymeric composition comprises a polymer having side chains along a backbone forming the polymer wherein at least two of the side chains contain an amino group (—NRH, —NH$_2$, —NRH$_2^+$, —NH$_3^+$). In one example embodiment, the polymer is a polyamide having amino substituted alkyl chains on one side of the polymer backbone. The crosslinking agent used in the polymeric composition contains at least two functional groups capable of reacting with the amino groups of the polymer used in the coating. In one example of the crosslinking agent used in the polymeric composition, the crosslinking agent is selected from the group consisting of phosphines having the general formula (A)$_3$P, wherein A is hydroxyalkyl, and mixtures thereof. One more specific example of the crosslinking agent used in the polymeric composition is tris(hydroxymethyl)phosphine. Specific non-limiting examples of the antimicrobial agent used in the polymeric composition include quaternary ammonium compounds, gentian violet compounds, substituted or unsubstituted phenols, biguanide compounds, iodine compounds, and mixtures thereof.

An article having an antimicrobial surface may be produced by a process according to the invention in which a polymer having at least two amino substituted side chains is mixed with a crosslinking agent to produce a polymer solution. The crosslinking agent contains at least two crosslinking functional groups which react and combine with amino groups on the polymer. The polymer solution is coated on at least a portion of a substrate to produce a crosslinked polymer coating on the substrate. In one version of the invention, an antimicrobial agent is added to the polymer solution before coating to entrap the antimicrobial agent in the crosslinked polymer coating on the substrate. In another version of the invention, a solution of an antimicrobial agent and a crosslinking agent (which may be the same as for the coating or a different crosslinking agent) is applied to the crosslinked polymer coating on the substrate after coating to immobilize the antimicrobial agent on the crosslinked polymer coating on the substrate. In yet another version of the invention, the crosslinked polymer coating on the substrate is treated after coating to create an anionic surface and a cationic antimicrobial agent is bonded to the crosslinked polymer coating on the substrate.

In an example embodiment of the invention, the versatile chemical methodology of the invention allows for the deposition of an antimicrobial polymeric composition on a polymeric substrate (e.g., polydimethylsiloxane, polyurethane, and polypropylene). The polymeric composition includes a two dimensional polymer having a backbone of repeating β-amino acid units with long aliphatic side-chain and free NH— and NH$_2$— substituents and may be synthesized by condensation of 2(5H)-furanone, or maleic acid derivatives (such as anhydride, esters, and so on) with a long-chain amine (e.g., tetradecylamine) and a polyamine (e.g., pentaethylenehexamine). Crosslinking of the two-dimensional polymer is undertaken with tris(hydroxymethyl)phosphine (the crosslinking agent), and an antimicrobial agent, such as quaternary ammonium compounds, gentian violet compounds, substituted or unsubstituted phenols, biguanide compounds, iodine compounds, and mixtures thereof, is incorporated into the crosslinked polymer coating. Various mechanisms are available for incorporating the antimicrobial agent into the crosslinked polymer coating, such as ionic bonding, covalent bonding and entrapment. However, it should be understood that the invention is not limited by the means for incorporating the antimicrobial agent into the crosslinked polymer coating.

Experimental studies indicate that when an antimicrobial agent, such as quaternary ammonium compounds, gentian violet compounds, substituted or unsubstituted phenols, biguanide compounds, iodine compounds, and mixtures thereof, is incorporated into the two-dimensional polymer and the polymer is crosslinked with the crosslinking agent, the resulting polymeric composition exhibits strong inhibitory activity against target pathogenic microorganisms. When the polymeric composition includes a mixture of different antimicrobial agents, synergistic antimicrobial activity greater than the sum of the activity of the individual antimicrobial agents alone is possible.

It is therefore an advantage of the present invention to provide an improved antimicrobial polymeric composition that may be easily applied to a substrate to produce an article which has excellent antimicrobial properties and which retains its antimicrobial properties in a permanent and non-leachable fashion when placed in an environment (e.g., bodily fluids) that may promote bacterial growth.

It is another advantage of the present invention to provide an improved antimicrobial polymeric composition that may be easily applied to a substrate for the prevention of medical device-related infections.

It is a further advantage of the present invention to provide an improved antimicrobial polymeric composition that may be easily applied to a substrate along with an anti-thrombogenic coating to prevent both clotting and bacterial infections.

These and other features, aspects, and advantages of the present invention will become better understood upon consideration of the following detailed description, drawings, and appended claims.

DETAILED DESCRIPTION OF THE INVENTION

The present invention is directed to a polymeric composition having antimicrobial properties. The polymeric composition comprises a crosslinked chemical combination of (i) a polymer having side chains along a backbone forming the polymer, at least two of the side chains containing an amino group, (ii) an antimicrobial agent selected from quaternary ammonium compounds, gentian violet compounds, substituted or unsubstituted phenols, biguanide compounds, iodine compounds, and mixtures thereof, and (iii) a crosslinking agent containing at least two functional groups capable of reacting with the amino groups. An article having a antimicrobial surface according to the invention comprises a substrate and a coating of the antimicrobial polymeric composition disposed on at least a portion of the substrate.

Figure 1A:
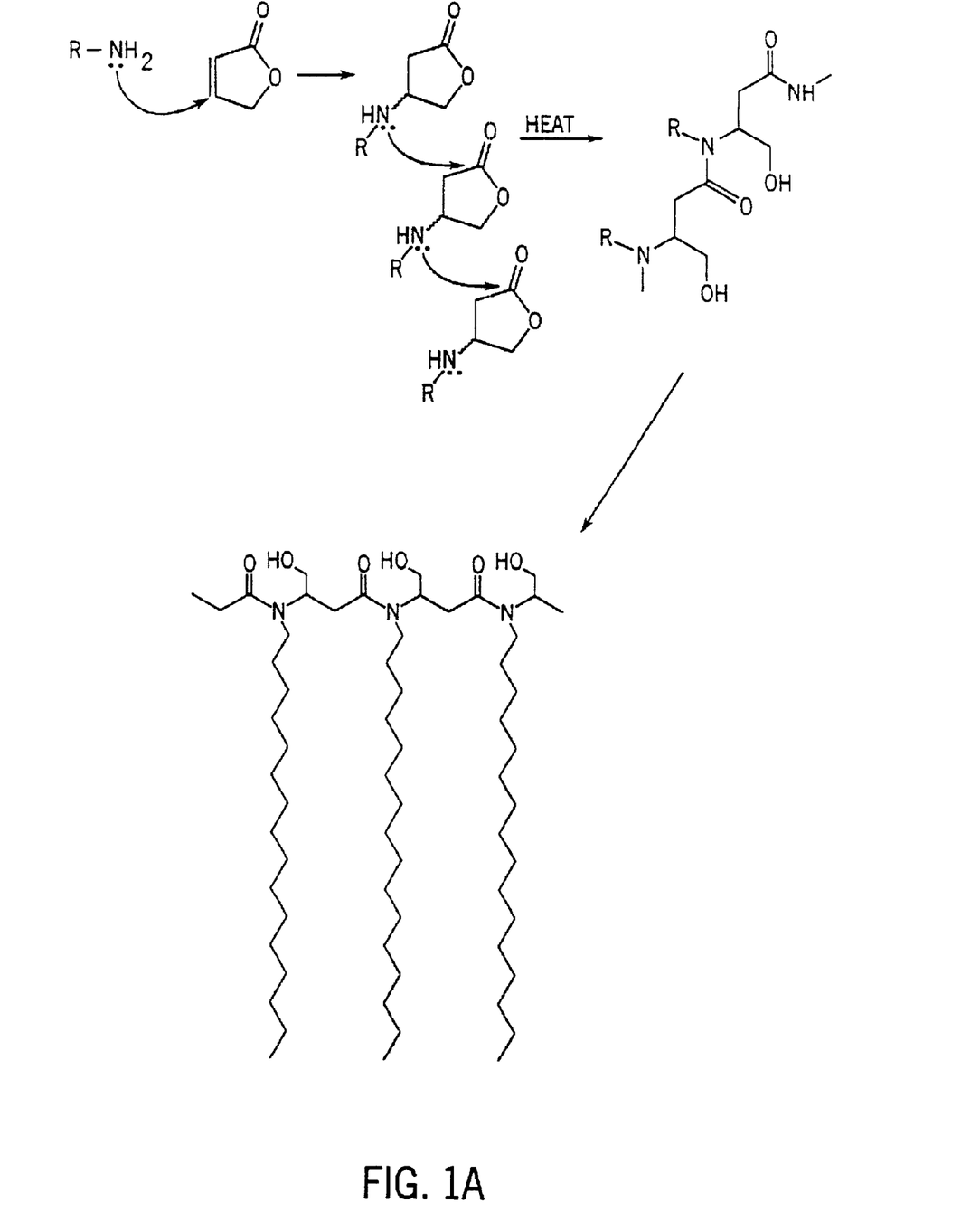
FIG. 1A shows a process for synthesizing a polyamide that is suitable for forming an antimicrobial polymeric composition coating in accordance with the present invention.
Figure 1B:
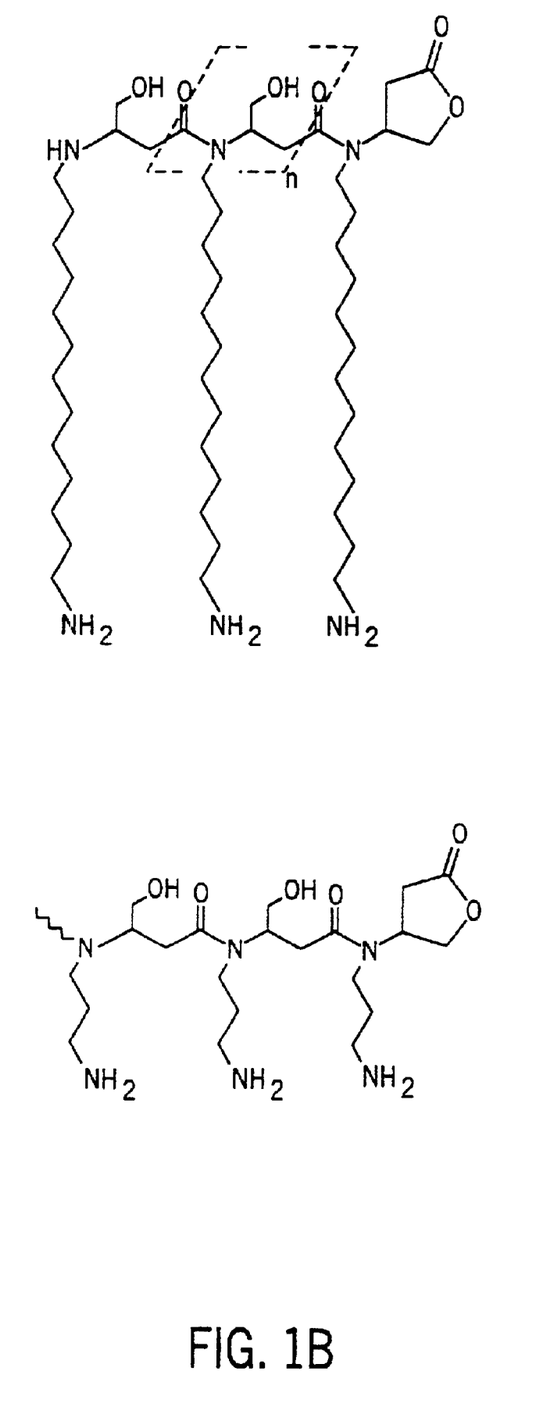
FIG. 1B shows example polyamides having amino groups that are suitable for forming the antimicrobial polymeric composition coating in accordance with the present invention.

The polymer used in the antimicrobial polymeric composition comprises a polymer having side chains along a backbone forming the polymer wherein at least two of the side chains contain an amino group (—NRH, —NH$_2$, —NRH$_2^+$, —NH$_3^+$). In one example embodiment of the polymer, the polymer is a polyamide synthesized using the polymerization reactions disclosed in U.S. Pat. No. 6,153,724, which are shown in FIG. 1A. Looking at FIG. 1A, it can be seen that the polyamide can be synthesized using an α,β-unsaturated gamma lactone, such as 2(5H)-furanone, as an agent to effect the regular, sequential alignment of side chains along a polyamide backbone. The furanone undergoes facile reaction with a primary amine by Michael-type addition to yield α,β-amino gamma lactone which then polymerizes to form a polyamide chain with the pendant side chain. Depending on the side group (R), the method can produce many different types of polyamides. When the R group is a polyamine (such as pentaethylenehexamine), a polymer having alkyl chains on one side and amino substituted alkyl chains on the other side of the polymer backbone and hydroxymethyl groups on the other side of the backbone is formed. See FIG. 1B. This example two-dimensional polymer has a backbone of repeating β-amino acid units with fatty alkyl (tetradecyl) and polyamine (derived from pentaethylenehexamine) side chains randomly distributed along the chain. By virtue of its amphithetic properties, the two-dimensional polymers are easily soluble in both water and most organic solvents (e.g., alcohols, tetrahydrofuran, chloroform, toluene, N,N-dimethylformamide, and the like).

One polyamide disclosed in U.S. Pat. No. 6,153,724 and useful in the present invention is formed by reacting an α,β-unsaturated lactone and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof; and (ii) reacting the intermediate reaction product and a polyamine to form the polyamide, wherein the second polyamine is selected from $R_2R_3NH$, $R_2NH_2$, $R_2R_3NH_2^+$, $R_2NH_3^+$ and mixtures thereof, wherein $R_2$ and $R_3$ can be the same or different and each contain an amino group (—NRH, —NH$_2$, —NRH$_2^+$, —NH$_3^+$) and between about 1 and 50 carbon atoms and are optionally substituted with heteroatoms oxygen, nitrogen, sulfur, and phosphorus and combinations thereof, wherein multiples of the R, $R_1$, $R_2$, and $R_3$ are in a vertically aligned spaced relationship along a backbone formed by the polyamide. In one example embodiment of the invention, R, $R_1$, $R_2$, and $R_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different.

Figure 2A:
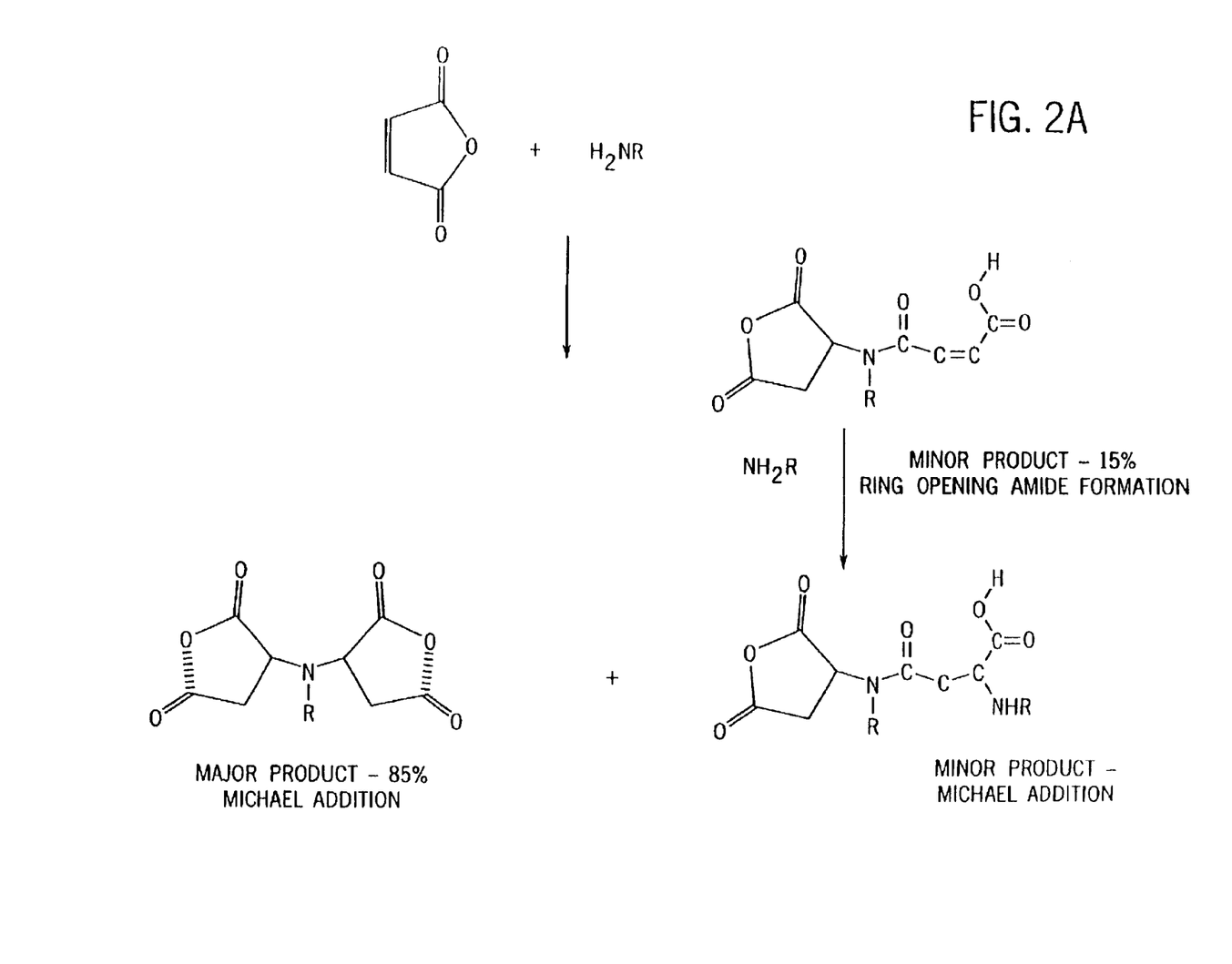
FIGS. 2A and 2B show a process for synthesizing another example polyamide having amino groups that are suitable for forming the antimicrobial polymeric composition coating in accordance with the present invention.
Figure 2B:
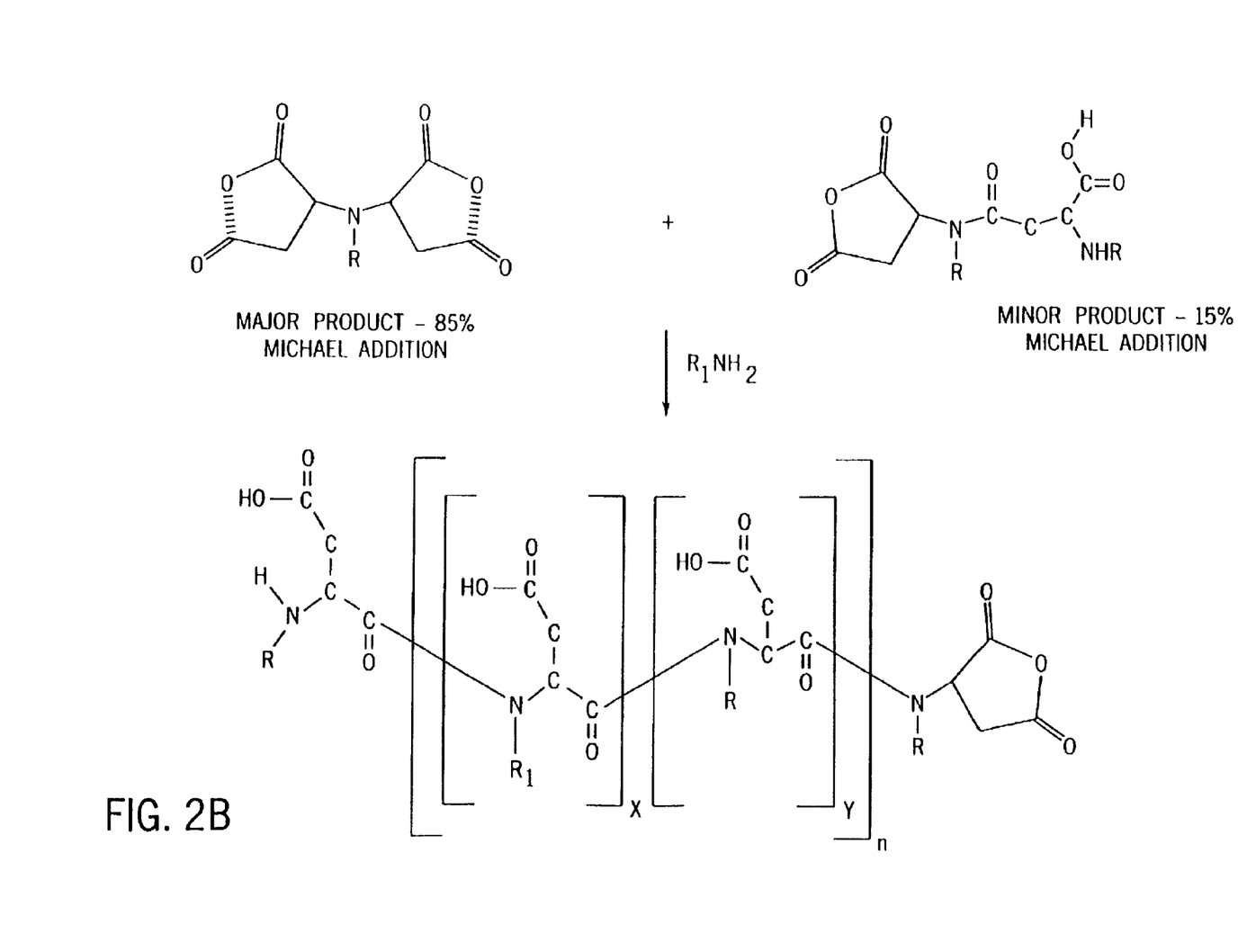

In another example of the polymer used in the antimicrobial polymeric composition, the polymer is a polyamide synthesized using the polymerization reaction disclosed in U.S. patent application Ser. No. 09/698,619 entitled "Two Dimensional Polyamides Prepared from Unsaturated Carboxylic Acids and Amines" filed on Oct. 27, 2000 by William F. McDonald et al., issued as U.S. Pat. No. 6,495,657, which is owned by the assignee of the present invention and is incorporated herein by reference. In this U.S. patent application, there is described a polymerization process in which a monomer selected from unsaturated carboxylic acids, esters of unsaturated carboxylic acids, anhydrides of unsaturated carboxylic acids, and mixtures thereof is reacted with a first amine to form an intermediate reaction product, and then the intermediate reaction product is reacted with a polyamine to form a polyamide wherein at least a portion of the side chains along a backbone forming the polyamide are amino substituted alkyl chains. See FIGS. 2A and 2B (wherein $R^1$ includes an amino group). The process for producing this polyamide involves reacting a monomer selected from unsaturated carboxylic acids, esters of unsaturated carboxylic acids, anhydrides of unsaturated carboxylic acids and mixtures thereof with a first amine to form an intermediate reaction product in the reaction mixture, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof. The reaction of the monomer and the first amine forms an intermediate reaction product in the reaction mixture. The intermediate reaction product is then reacted with a second amine selected from $R_2R_3NH$, $R_2NH_2$, $R_2R_3NH_2^+$, $R_2NH_3^+$ and mixtures thereof, wherein $R_2$ and $R_3$ can be the same or different and each contain an amino group (—NRH, —NH$_2$, —NRH$_2^+$, —NH$_3^+$) and each contain between about 1 and 50 carbon atoms and are optionally substituted with heteroatoms oxygen, nitrogen, sulfur, and phosphorus and combinations thereof. The reaction of the intermediate reaction product with the second amine forms the polyamide in the reaction mixture. The polyamide may then be separated from the reaction mixture. A polyamide produced in accordance with the method of the invention includes multiples of the R, $R_1$, $R_2$, and $R_3$ groups in vertically aligned spaced relationships along a backbone formed by the polyamide.

Suitable unsaturated carboxylic acids, esters of unsaturated carboxylic acids, and anhydrides of unsaturated carboxylic acids for use as the monomer in this polymerization process have for example from 3 to 18 carbon atoms in the molecule. Of this group of acids, the monocarboxylic acid, acrylic acid, and the dicarboxylic acid, maleic acid, are preferred. Of this group of esters, maleic acid monoesters (such as maleic acid monoethyl ester) are preferred. A non-limiting example of anhydrides of the unsaturated carboxylic acids is maleic anhydride. In one example embodiment of the invention, R, $R_1$, $R_2$, and $R_3$ may be selected from alkyl, alkenyl, alkynyl, cycloalkyl, aryl, aralkyl, hydroxyl, nitrile, carboxyl, sulfate, phosphate, sulfonyl trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different.

The crosslinking agent used in the coating contains at least two functional groups capable of reacting with the amino groups of the polymer used in the coating. Example crosslinking agents include polyaldehydes such as glutaraldehyde. It has also been discovered that the polymer can be crosslinked using a phosphine crosslinking agent having the general formula $(A)_3P$ and mixtures thereof, wherein A is hydroxyalkyl. The A groups of the phosphine crosslinking agent undergo a spontaneous Mannich-type reaction with amino groups on the polymer under mild conditions (pH ~7, aqueous or organic media, room temperature, 2–24 hours). This results in the formation of an aminomethyl-phosphine linkage (N—CH$_2$—P—CH$_2$—N) which is much less susceptible to enzyme deactivation and hydrolysis at a low pH than other known crosslinkages.

The phosphine crosslinking agent has many other important features. For example, the phosphine crosslinking agent has a high reactivity to amino groups under mild conditions (room temperature, in aqueous or organic media, pH 2–9, and a pot life extending to several hours). The resulting Mannich base type products formed from the phosphine crosslinking agent show a higher stability over that provided by glutaraldehyde in that a polymer crosslinked by glutaraldehyde containing 10% phosphine crosslinking agent was found to withstand low pH (pH 2–3) and high temperature conditions (boiling water poured into a large beaker followed by the addition of the coated plates without additional heating for 30 minutes) without deterioration. The phosphine crosslinking agent is unusually highly reactive with a number of other important functional groups such as urea, biguanide, and ortho-substituted or para-substituted phenols, which allows for covalent bonding with numerous antimicrobial agents including nearly all chlorophenol type disinfectants, such as chlorhexidine and methyl violet 2B (N-dimethyl-Gentian violet), which are not generally reactive to other crosslinking materials. In addition, the phosphine crosslinking agent offers the benefits of operational simplicity, good biocompatibility, and low cost. The phosphine crosslinking agent can also react with the substrate to create tightly bound anchors between the polyamide coating and the substrate. Non-limiting examples of phosphine crosslinking agents include tris(hydroxymethyl)phosphine, tris(1-hydroxyethyl)phosphine, and tris(1-hydroxypropyl) phosphine. In certain circumstances, it may be cost effective to form the phosphine crosslinking agent in situ such as by the reaction of tetrakis-(hydroxymethyl)phosphonium chloride and triethylamine.

The amount of crosslinking agent and the amount of polymer used to produce the antimicrobial polymeric composition can be varied depending upon the particular crosslinking agent utilized, the reaction conditions and the particular product application contemplated. For example, the ratio of A groups in the phosphine crosslinking agent to the total of amount of amino groups in the polyamide can be varied to achieve a predetermined level of crosslinking. Typically, the A groups in the phosphine crosslinking agent to the total of amount of amino groups in the polymer is about 30% to provide acceptable crosslinking. In one version of the invention, enough phosphine crosslinking agent is added to the polyamide such that at least 30% of the available amino groups in the polymer are crosslinked by the A groups in the phosphine crosslinking agent. This percentage or amount of phosphine crosslinker can be varied to obtain antimicrobial polymeric composition coatings with the desired crosslink density.

The antimicrobial agent used in the polymeric composition may be selected from quaternary ammonium compounds, gentian violet compounds, substituted or unsubstituted phenols, biguanide compounds, iodine compounds, and mixtures thereof.

Non-limiting illustrative quaternary ammonium compounds include alkyl-dimethyl-benzylammonium chloride, alkyl-dimethyl-ethylbenzylammonium chloride, dodecyl-dimethyl-3,4-dichlorobenzylammonium chloride, dodecyl-di-(2-hydroxyethyl)-benzylammonium chloride, dodecyl-di-(2-hydroxyethyl)-benzylammonium pentachlorophenolate, dodecyl-di-(2-hydroxyethyl)-benzylammonium 4-methylbenzoate, dodecyl-dimethyl-phenoxyethylammonium bromide, 4-diisobutyl-phenoxyethoxyethyl-dimethylbenzylammonium chloride, 4-diisobutyl-cresoxyethoxyethyl-dimethylbenzylammonium chloride, dimethyl-didecylammonium chloride, cetyl-trimethylammonium bromide, dodecyl-pyridinium chloride, cetyl pyridinium chloride, dodecyl-isoquinolinium chloride, decamethylene-bis-4-aminoquinaldinium dichloride, alpha-(p-tolyl)-dodecyl-trimethyl-ammonium methosulphate, (dodecanoyl-N-methylaminoethyl)-(phenylcarbamoylmethyl)-dimethylammonium chloride, and mixtures thereof. One preferred quaternary ammonium compound is cetyl pyridinium chloride (1-hexadecylpyridinium chloride).

Non-limiting illustrative gentian violet compounds include gentian violet and dimethyl gentian violet.

Non-limiting illustrative substituted or unsubstituted phenols include phenol, mono- and poly-chlorophenols, cresols, 4-chloro-3-methylphenol, 3,5-dimethyl-4-chlorophenol, thymol, 4-chlorothymol, 4-t-amylphenol, saligenin, 4-n-hexylresorcinol, carvacrol, 2-phenylphenol, 2-benzyl-4-chlorophenol, 2,2'-dihydroxy-5,5'-dichlorodiphenylmethane, 2,2'-dihydroxy-3,3',5,5',6,6'-hexachlorodiphenylmethane, 2,2'-dihydroxy-5,5'-dichlorodiphenyl sulphide, 2,2'-dihydroxy-3,3',5,5'-tetrachlorodiphenyl sulphide, 2-hydroxy-2',4,4'-trichlorodiphenyl ether, dibromosalicyl and mixtures thereof. One preferred substituted phenol is 3,5-dimethyl-4-chlorophenol (chloroxylenol). Another preferred substituted phenol is thymol (isopropyl-m-cresol). Yet another preferred substituted phenol is triclosan (5-chloro-2-(2,4-dichlorophenoxy)phenol).

Non-limiting illustrative biguanide compounds include compounds of the general formula (I), (II) or (III) given below:

In the formulas (I), (II) and (III), R is an alkyl group, an aminoalkyl group, a phenyl group, an alkylphenyl group, a halophenyl group, a hydroxyphenyl group, a methoxyphenyl group, a carboxyphenyl group, a naphthyl group or a nitrile group; R' is a hydrogen atom or an alkyl group; and m and n each is a positive integer, preferably an integer within the range of 2 to 10. A preferred example of a suitable biguanide compound is chlorhexidine, also known as 1,6-bi($N^5$-p-chlorophenyl-$N^1$-biguanido)hexane.

Non-limiting illustrative iodine compounds include potassium iodate, potassium iodide, iodine complexes (such as KI:$I_2$ and polyvinylpyrrolidone:iodine) and iodine (which as described herein will be considered an "iodine compound"). A preferred example of an iodine compound is iodine.

The amount and/or type of the antimicrobial agent used will vary depending on the particular material employed and ultimate desired effect. For instance, the amount and/or type of the antimicrobial agent which is used in a particular application may vary depending on the type and amount of contamination which is likely to occur and the size of the antimicrobial surface present in the article. For example, certain antimicrobial agents may be highly effective against most bacteria, but less effective against other bacteria.

While the amount of each antimicrobial agent used to coat the medical device may vary to some extent, the amount of each antimicrobial agent must be at least a sufficient amount to form an effective concentration to kill or suppressing the replication of viruses, to kill or inhibit the growth of bacterial microorganisms, or to kill or suppress the replication of fungi. The term "effective concentration" means that a sufficient amount of the antimicrobial agent is added to decrease, prevent or inhibit the growth of bacterial, viral, and/or fungal organisms. The amount will vary for each antimicrobial agent and it is within the skilled artisan's ability to relatively easily determine an effective concentration for each antimicrobial agent. In addition, an upper limit of the concentration of the antimicrobial agent may exist under certain circumstances such as when the solubility limit of the antimicrobial agent in the polymer coating is reached.

The antimicrobial polymeric composition may be applied to any substrate that is considered useful in applications where antimicrobial properties are advantageous. For instance, an article having antimicrobial properties and useful as a medical device may include a substrate comprising a polymeric material conventionally used to fabricate articles commonly used in contact with bodily fluids. In this example, suitable polymeric material may be selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof. The particular substrate selected does not constitute a critical aspect of the invention other than to serve as a support substrate for the antimicrobial polymeric coating composition.

An article having an antimicrobial surface according to the invention may be prepared using various methods as follows. In a first method for preparing an article having an antimicrobial surface according to the invention, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2^+$, —NH$_3^+$) is then prepared in a suitable solvent, such as isopropanol. The polymer concentration can vary and is typically from 1 to 5% depending on the desired coating concentration. A crosslinking agent or a mixture of crosslinking agents is then added to the polymer solution. Each crosslinking agent should contain at least two functional groups capable of reacting with the amino groups of the polymer. Non-limiting examples of crosslinking agents include polyaldehydes, such as glutaraidehyde, phosphines having the general formula (A)$_3$P, wherein A is hydroxyalkyl, and mixtures thereof. One example mixture of crosslinking agents includes 50% glutaraldehyde+80% tris (hydroxymethyl)phosphine (5:1, v/v). The phosphine crosslinking agent may also be formed in situ such as by the reaction of tetrakis-(hydroxymethyl)-phosphonium chloride and triethylamine.

The polymer/crosslinking agent solution is then applied to a substrate and the substrate may be heated or baked in an oven at 125° C. for four hours to complete the crosslinking process and create a crosslinked polymeric coating on the substrate. This step may be repeated if necessary. Typically, the coatings are applied using a dipping process. However, the coatings can be spin coated, brushed, sprayed, sponged, or the like onto the substrate. Immobilization of an antimicrobial on the crosslinked polymer coating may then be accomplished by (a) preparing a coating solution of (i) an antimicrobial agent selected from gentian violet compounds, substituted or unsubstituted phenols, biguanide compounds, and mixtures thereof, (ii) a crosslinking agent containing at least two crosslinking functional groups capable of reacting with the amino groups (e.g., polyaldehydes, such as glutaraldehyde, phosphines having the general formula (A)$_3$P, wherein A is hydroxyalkyl, and mixtures thereof), and (iii) optionally a solvent such as isopropanol; and (b) applying the coating solution to the crosslinked polymer coating on the substrate. Without intending to be bound by theory, it is believed that the antimicrobial agent forms a covalent bond with the polymer and/or the crosslinking agent(s).

In a second method for preparing an article having an antimicrobial surface according to the invention, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2^+$, —NH$_3^+$) is then prepared in a suitable solvent, such as isopropanol. The polymer concentration can vary and is typically from 1 to 5% depending on the desired coating concentration. A crosslinking agent or a mixture of crosslinking agents is then added to the polymer solution. Each crosslinking agent should contain at least two functional groups capable of reacting with the amino groups of the polymer. Non-limiting examples of crosslinking agents include polyaldehydes, such as glutaraldehyde, phosphines having the general formula (A)$_3$P, wherein A is hydroxyalkyl, and mixtures thereof. The phosphine crosslinking agent may also be formed in situ such as by the reaction of tetrakis-(hydroxymethyl)phosphonium chloride and triethylamine. An antimicrobial agent selected from quaternary ammonium compounds, gentian violet compounds, substituted or unsubstituted phenols, biguanide compounds, iodine compounds, and mixtures thereof, is then added to the polymer solution.

The polymer/crosslinking agent/antimicrobial agent solution is then applied to a substrate and the substrate may be heated or baked in an oven at 125° C. for four hours to complete the crosslinking process and create an antimicrobial crosslinked polymeric coating on the substrate. This step may be repeated if necessary. Typically, the coatings are applied using a dipping process. However, the coatings can be spin coated, brushed, sprayed, sponged, or the like onto the substrate. Without intending to be bound by theory, it is believed that the antimicrobial agent is entrapped in the crosslinked polymer coating on the substrate surface.

In a third method for preparing an article having an antimicrobial surface according to the invention, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2^+$, —NH$_3^+$) is then prepared in a suitable solvent, such as isopropanol. The polymer concentration can vary and is typically from 1 to 5% depending on the desired coating concentration. A crosslinking agent or a mixture of crosslinking agents is then added to the polymer solution. Each crosslinking agent should contain at least two functional groups capable of reacting with the amino groups of the polymer. Non-limiting examples of crosslinking agents include polyaldehydes, such as glutaraldehyde, phosphines having the general formula (A)$_3$P, wherein A is hydroxyalkyl, and mixtures thereof. The phosphine crosslinking agent may also be formed in situ such as by the reaction of tetrakis-(hydroxymethyl)phosphonium chloride and triethylamine. One example mixture of crosslinking agents includes 50% glutaraldehyde+80% tris (hydroxymethyl)phosphine (5:1, v/v).

The polymer/crosslinking agent solution is then applied to a substrate and the substrate may be heated or baked in an oven at 125° C. for four hours to complete the crosslinking process and create a crosslinked polymeric coating on the substrate. This step may be repeated if necessary. Typically, the coatings are applied using a dipping process. However, the coatings can be spin coated, brushed, sprayed, sponged, or the like onto the substrate. Immobilization of an antimicrobial on the crosslinked polymer coating may then be accomplished by (a) treating at least a portion of the crosslinked polymer coating with a charge derivatization agent to create a negative charge on the portion of the crosslinked polymer coating, and (b) applying a cationic antimicrobial agent selected from quaternary ammonium compounds, gentian violet compounds, biguanide compounds, iodine compounds, and mixtures thereof, to the portion of the crosslinked polymer coating. While numerous charge derivatization agents are suitable for use in the method of the invention, one example embodiment of the third method of the invention involves the preparation of a sulfonate rich surface by charge derivatization of the polymer coating layer using 2-sulfobenzoic acid anhydride.

Without intending to be bound by theory, it is believed that the antimicrobial agent forms an ionic bond with the treated crosslinked polymer coating.

Any of the antimicrobial coated substrates produced by the above methods may be further treated with an iodine compound. For example, the antimicrobial coated substrate may be impregnated in aqueous 1% $KI:I_2$ complex (Burke's iodine) for several minutes. This typically results in dark brown iodine surface. It has been discovered that antimicrobial coated substrates produced by the above methods are good iodophores to keep iodine on the surface for a period longer than 2 weeks, which is comparable to polyvinylpyrrolidone complexed iodine.

EXAMPLES

The following examples serve to further illustrate the invention. The Control Example details the preparation of a substrate having a crosslinked polyamide coating. Examples 1–16 detail the preparation of substrates having different antimicrobial crosslinked polyamide coatings in accordance with the invention. The examples are not intended to limit the invention in any way.

Control Example

A. Preparation of a Polyamide with Side Chains

A polymer with side chains was prepared as follows. First, 1.0 moles (144.1 grams) of maleic acid mono-ethyl ester was dissolved in 100 grams of isopropanol in a break away resin kettle. The kettle containing the maleic acid mono-ethyl ester/isopropanol solution was then cooled in an ice bath with agitation. Second, 0.5 moles (160.7 grams) of commercially available tetradecylamine was dissolved in 250 grams of isopropanol and added slowly to the cooled maleic acid mono-ethyl ester solution with stirring. A Michael-type addition reaction product began to precipitate within 5 minutes. The tetradecylamine addition required about two hours with ice bath conditions being maintained throughout. Third, 58.1 grams (0.25 moles) of commercially available pentaethylenehexamine were added drop wise to the reaction solution over a two hour period. The reaction is removed from the ice bath at the end of the monomer addition and stirred for an additional 2 hours. The amount of pentaethylene-hexamine charged is determined from the monomer charge from the formation of intermediate. After complete addition of the pentaethylene-hexamine, the reaction kettle was removed from the cold bath with continuous stirring for another 2 hours.

B. Preparation of a Substrate

Before application of a polymer coating to a substrate, the surface of the substrate was modified. Substrate surface modification was accomplished by adding 2 milliliters of 3-(2-(2-aminoethylamino)ethylamino)propyl-trimethoxysilane and 0.1 milliliters of glacial acetic acid to 50 milliliters of isopropanol. A polydimethylsiloxane substrate was then dip coated in this solution followed by a 125° C. cure cycle in a forced air oven for 15 minutes.

C. Preparation of a Substrate Having a Crosslinked Polyamide Coating

A 3% solution of the polyamide with side chains prepared above was prepared in isopropanol. A polymer coating solution was then prepared by mixing 50 milliliters of the 3% solution of the polyamide, 100 milligrams of hydroquinone, 50 milligrams of Triton™ X-100 brand non-ionic surfactant, 1.5 milliliters of 50% glutaraldehyde, 0.1 milliliters of triethylamine, and 0.15 milliliters of 80% tetrakis(hydroxymethyl)-phosphonium chloride. The surface modified substrate prepared above was then dipped in the polymer coating solution two times and heated by hot air at 120°–150° C. for 1 minute after each dip. The coated substrate was then hung in a 125° C. oven to cure for 2 hours.

Example 1

Preparation of a Substrate Having a Crosslinked Polyamide Coating Including a Quaternary Ammonium Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated for 1 hour in a solution of 0.75 grams of 2-sulfobenzoic anhydride, 150 milliliters of 50 mM phosphate buffered saline (pH=7.4), 10 milliliters of isopropanol, 0.1 grams of dimethylaminopyridine, and 0.45 milliliters of triethylamine (adjust pH to 7.4). The coated substrate was then water rinsed and air dried.

The coated substrate was then incubated at room temperature for 1 hour in a solution of 1.0 grams of cetyl pyridinium chloride, 100 milliliters of water and 10 milliliters of isopropanol. The coated substrate was then air dried, water rinsed by soaking for 15 minutes, and then air dried.

Example 2

Preparation of a Substrate Having a Crosslinked Polyamide Coating Including a Gentian Violet Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated for 1 hour in a solution of 0.75 grams of 2-sulfobenzoic anhydride, 150 milliliters of 50 mM phosphate buffered saline (pH=7.4), 10 milliliters of isopropanol, 0.1 grams of dimethylaminopyridine, and 0.45 milliliters of triethylamine (adjust pH to 7.4). The coated substrate was then water rinsed and air dried.

The coated substrate was then incubated at room temperature overnight in a solution of 350 milligrams of dimethyl gentian violet and 100 milliliters of water, rinsed with distilled water until the washings were colorless, and then air dried.

Example 3

Preparation of a Substrate Having a Crosslinked Polyamide Coating Including a Gentian Violet Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute. The coated substrate was then incubated for 16 hours at room temperature in a solution of 50 milliliters of 0.3% dimethylgentian violet, 150 milliliters of tris (hydroxymethyl)-phosphine and 10 milliliters of isopropanol. The substrates were then rinsed with water to remove excess dye, and air dried.

Example 4

Preparation of a Substrate Having a Crosslinked Polyamide Coating Including a Substituted Phenol Compound A 3% solution of the polyamide with side chains as prepared in the Control Example was prepared in isopropanol. A polymer coating solution was then prepared by mixing 55 milliliters of the 3% polymer solution in isopropanol, 198 milligrams of thymol, 1.5 milliliters of 50% glutaraldehyde, 0.15 milliliters of 80% tetrakis(hydroxymethyl)-phosphonium chloride, and 0.1 milliliters of triethylamine. A surface modified substrate as prepared in the Control Example was then dipped in the polymer coating solution two times and heat gun dried after each dip. The coated substrate was then cured by hanging in a 125° C. oven for 16 hours. The coated substrate was then washed by incubating in 10 mM phosphate buffered saline (pH=7.4) for 1 hour, rinsed two times for 15 minutes with distilled water, and air dried.

Example 5

Preparation of a Substrate Having a Crosslinked Polyamide Coating Including a Substituted Phenol Compound A 3% solution of the polyamide with side chains as prepared in the Control Example was prepared in isopropanol. A polymer coating solution was then prepared by mixing 55 milliliters of the 3% polymer solution in isopropanol, 208 milligrams of triclosan, 1.5 milliliters of 50% glutaraldehyde, 0.2 milliliters of 80% tetrakis(hydroxymethyl)-phosphonium chloride, and 0.2 milliliters of triethylamine. A surface modified substrate as prepared in the Control Example was then dipped in the polymer coating solution two times and heat gun dried after each dip. The coated substrate was then cured by hanging in a 125° C. oven for 16 hours. The coated substrate was then washed by incubating in 10 mM phosphate buffered saline (pH=7.4) for 1 hour, rinsed two times for 15 minutes with distilled water, and air dried.

Example 6

Preparation of a Substrate Having a Crosslinked Polyamide Coating Including a Biguanide Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated for 1 hour in a solution of 0.75 grams of 2-sulfobenzoic an hydride, 150 milliliters of 50 mM phosphate buffered saline (pH=7.4), 10 milliliters of isopropanol, 0.1 grams of dimethylaminopyridine, and 0.45 milliliters of triethylamine (adjust pH to 7.4). The coated substrate was then water rinsed and air dried.

The coated substrate was then incubated at room temperature for 2 hours in a solution of 0.6 grams of chlorhexidine, 80 milliliters of water, 10 milliliters of isopropanol, and enough triethylamine to adjust the pH to 3.8.

Example 7

Preparation of a Substrate Having a Crosslinked Polyamide Coating Including a Biguanide Compound A 3% solution of the polyamide with side chains as prepared in the Control Example was prepared in isopropanol. A polymer coating solution was then prepared by mixing 55 milliliters of the 3% polymer solution in isopropanol, 215 milligrams of chlorhexidine, 1.5 milliliters of 50% glutaraldehyde, and 0.15 milliliters of 80% tetrakis(hydroxymethyl)-phosphonium chloride. A surface modified substrate as prepared in the Control Example was then dipped in the polymer coating solution two times and heat gun dried after each dip. The coated substrate was then cured by hanging in a 125° C. oven for 3 hours. After curing, boiled water was poured over the substrates in a beaker. Without further heating, the substrates were periodically and gently stirred for 15 minutes.

Example 8

Preparation of a Substrate Having a Crosslinked Polyamide Coating Including an Iodine Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant: in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated for 1 hour in a solution of 0.75 grams of 2-sulfobenzoic anhydride, 150 milliliters of 50 mM phosphate buffered saline (pH=7.4), 10 milliliters of isopropanol, 0.1 grams of dimethylaminopyridine, and 0.45 milliliters of triethylamine (adjust pH to 7.4). The coated substrate was then water rinsed and air dried.

A 1% KI:$I_2$ complex (Burke's Iodine) was then prepared as follows. One gram of potassium iodide (KI) and 1 gram of iodine were placed in a mortar and ground with a pestle for 1 minute. Then 1 milliliter of distilled water was added and ground. Then 5 milliliters of water were added and ground until all material was in solution. Ten milliliters of water were added, and mixed and poured into an amber bottle. The mortar and pestle were rinsed to bring the total volume to 100 milliliters.

The coated substrate was then incubated in the prepared 1% KI:$I_2$ solution at room temperature for 10 minutes. The substrates were water rinsed until the washings were colorless. The rinsed substrates were air dried for 2 hours, and then stored in a petri dish wrapped with aluminum foil to avoid exposure to light.

Example 9

Preparation of a Substrate Having a Crosslinked Polyamide Coating Including a Gentian Violet and an Iodine Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated for 1 hour in a solution of 0.75 grams of 2-sulfobenzoic anhydride, 150 milliliters of 50 mM phosphate buffered saline (pH=7.4), 10 milliliters of isopropanol, 0.1 grams of dimethylaminopyridine, and 0.45 milliliters of triethylamine (adjust pH to 7.4). The coated substrate was then water rinsed and air dried.

The coated substrate was then incubated in a solution containing 200 milligrams of dimethyl gentian violet and 100 milliliters of water for 5 hours. The coated substrate was then air dried, water rinsed to remove excess dye, and air dried.

The coated substrate was then incubated in the 1% KI:$I_2$ solution as prepared in Example 8 at room temperature for 10 minutes. The substrates were water rinsed until the washings were colorless. The rinsed substrates were air dried for 2 hours, and then stored in a petri dish wrapped with aluminum foil to avoid exposure to light.

Example 10

Preparation of a Substrate Having a Crosslinked Polyamide Coating Including a Biguanide and a Substituted Phenol Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated at room temperature for 75 minutes in a solution of 1 milliliter of 80% tetrakis(hydroxymethyl)-phosphonium chloride, 0.5 milliliters of triethylamine, 442 milligrams of dimethylchlorophenol, 1.32 grams of chlorhexidine, 40 milliliters of water, and 10 milliliters of isopropanol. The coated substrate was then rinsed under running distilled water for 3 minutes.

Example 11

Preparation of a Substrate Having a Crosslinked Polyamide Coating Including a Biguanide and a Substituted Phenol Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated at room temperature for 75 minutes in a solution of 1 milliliter of 80% tetrakis(hydroxymethyl)-phosphonium chloride, 0.5 milliliters of triethylamine, 445 milligrams of dimethylchlorophenol, 0.69 grams of chlorhexidine, 40 milliliters of water, and 10 milliliters of isopropanol. The coated substrate was then rinsed under running distilled water for 3 minutes.

Example 12

Preparation of a Bandage Including a Biguanide and a Substituted Phenol Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A sample of a commercially available gauze (Johnson & Johnson 'Nu Gauze'—Rayon/polyester formed fabric) was then dipped in the polymer coating solution.

The coated gauze was then incubated for 75 minutes at room temperature in a solution of 247 milligrams of dimethylchlorophenol, 681 milligrams of chlorhexidine, 10 milliliters of isopropanol, and 40 milliliters of dimethoxyethane. The coated gauze was then rinsed under running distilled water for 3 minutes.

Example 13

Preparation of a Substrate Having a Crosslinked Polyamide Coating Including a Biguanide and a Substituted Phenol Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated for 30 minutes in a solution of 1 milliliter of 80% tetrakis(hydroxymethyl)-phosphonium chloride, 220 milligrams of dimethylchlorophenol, 360 milligrams of chlorhexidine, 55 milligrams of hydroquinone, 80 milliliters of water, 20 milliliters of isopropanol, and 1 milliliter of triethylamine. The coated substrate was then dried with hot air of 120°–150° C. for 1 minute and then rinsed with running distilled water for 1 minute.

Example 14

Preparation of a Substrate Having a Crosslinked Polyamide Coating Including a Biguanide, a Substituted Phenol and an Iodine Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated at room temperature for 75 minutes in a solution of 1 milliliter of 80% tetrakis(hydroxymethyl)-phosphonium chloride, 0.5 milliliters of triethylamine, 442 milligrams of dimethylchlorophenol, 1.32 grams of chlorhexidine, 40 milliliters of water, and 10 milliliters of isopropanol. The coated substrate was then rinsed under running distilled water for 3 minutes.

The coated substrate was then incubated in the 1% KI:I$_2$ solution as prepared in Example 8 at room temperature for 10 minutes. The substrates were water rinsed until the washings were colorless. The rinsed substrates were air dried for 2 hours, and then stored in a petri dish wrapped with aluminum foil to avoid exposure to light.

Example 15

Preparation of a Substrate Having a Crosslinked Polyamide Coating Including a Biguanide, a Substituted Phenol and an Iodine Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated at room temperature for 75 minutes in a solution of 1 milliliter of 80% tetrakis(hydroxymethyl)-phosphonium chloride, 0.5 milliliters of triethylamine, 445 milligrams of dimethylchlorophenol, 0.69 grams of chlorhexidine, 40 milliliters of water, and 10 milliliters of isopropanol. The coated substrate was then rinsed under running distilled water for 3 minutes.

The coated substrate was then incubated in the 1% KI:I$_2$ solution as prepared in Example 8 at room temperature for 10 minutes. The substrates were water rinsed until the washings were colorless. The rinsed substrates were air dried for 2 hours, and then stored in a petri dish wrapped with aluminum foil to avoid exposure to light.

Example 16

Preparation of a Substrate Having a Crosslinked Polyamide Coating Including a Biguanide, a Substituted Phenol and a Gentian Violet Compound A 3% solution of the polyamide with side chains as prepared in the Control Example was prepared in isopropanol. A polymer coating solution was then prepared by mixing 110 milliliters of the 3% solution of the polyamide, 4 milliliters of a 50 mg./ml. hydroquinone in isopropanol solution, 1 milliliter of 50 mg./ml. Triton™ X-100 brand non-ionic surfactant in isopropanol, 3 milliliters of 50% glutaraldehyde, 0.4 milliliters of triethylamine, and 0.4 milliliters of 80% tetrakis(hydroxymethyl)-phosphonium chloride. A surface modified substrate as prepared in the Control Example was then dipped in the polymer coating solution and heated by hot air at 120°–150° C. for 1 minute.

The coated substrate was then incubated at room temperature for 30 minutes in a solution of 1 milliliter of 80% tetrakis(hydroxymethyl)-phosphonium chloride, 1 milliliter of triethylamine, 220 milligrams of dimethylchlorophenol, 360 milligrams of chlorhexidine, 55 milligrams of hydroquinone, 80 milliliters of water, and 20 milliliters of isopropanol. The coated substrate was then heat gun dried at 120°–150° C. for 1 minute and rinsed under running distilled water for 1 minute. The coated substrate was then incubated in a solution of 50 milliliters of 0.3% dimethylgentian violet and 0.1 milliliters of tris(hydroxymethyl)-phosphine at room temperature for 2 hours. The substrates were water rinsed until the washings were colorless, and air dried.

Example 17

Antimicrobial Activity Assay

The selection of target microorganisms for examining the antimicrobial activity of the coated polydimethylsiloxane substrates produced in the Control Example and Examples 1–16 was based on the potential human pathogenic microorganisms, which include gram positive bacteria, *Bacillus subtilis* and *Staphylococcus aureus*; gram negative bacteria, *E. coli* and *Pseudomonas aeruginosa*; and yeast, *Candida albicans*. Broth cultures were prepared for each microorganism. Bacteria, *Bacillus subtilis, Staphylococcus aureus, E. coli* and *Pseudomonas aeruginosa* were grown in 50 milliliters of sterile tryptic soy broth in a 500 milliliter baffle flask at 200 rpm. The cultures were grown at 37° C. overnight, and used for antimicrobial activity assay plates and stock culture. The yeast, *Candida albicans* was cultivated in 50 milliliters of sterile yeast malt broth in a 250 milliliter baffle flask at 25–28° C. for 1 day and used for the activity assay plates and stock culture.

Antimicrobial activity assay plates were then prepared. Yeast malt agar and tryptic soy agar were autoclaved for 20 minutes. The sterile molten agar was allowed to cool to 42–45° C. The prepared broth cultures of the target microorganisms were inoculated to a final concentration of 5% (v/v). The broth cultures were mixed to obtain a homogeneous suspension, and a 20 milliliter aliquot of culture mixed agar media was poured into sterile plastic petri dishes. The agar was allowed to solidify, and dishes not to be used immediately were stored at 4° C.

The coated polydimethylsiloxane substrates produced in the Control Example and Examples 1–18 were placed on the prepared agar plates. After incubation at 30° C. for *Candida albicans* and 37° C. for the other microorganisms, respectively for 1–2 days, a clear zone of growth inhibition surrounding the coated substrates was visible against a partially opaque background of growth. The degree of inhibition was scored using the following point system shown in Table 1. (When the inhibition zone was hazy, the inhibition grade was ranked one lower degree.) The results are shown in Table 2.

TABLE 1

| Score | Score Description |
| --- | --- |
| 0 | No inhibition |
| ½ | Inhibition, but not clearly measurable. |
| 1 | Clearly observable inhibition wherein the diameter of the inhibition zone is in the range of 11–13 millimeters |
| 1½ | Half of a Degree between 1 and 2 |
| 2 | Clearly observable inhibition wherein the diameter of the inhibition zone is in the range of 14–16 millimeters |
| 3 | Clearly observable inhibition wherein the diameter of the inhibition zone is in the range of 17–20 millimeters |
| 4 | Clearly observable inhibition wherein the diameter of the inhibition zone is over 21 millimeters |

TABLE 2

| Example Tested | Patterns of Linkage | Staphylococcus aureus | Pseudomonas aeruginosa | Candida albicans | E. coli | Bacillus subtilis |
| --- | --- | --- | --- | --- | --- | --- |
| Control | N/A | 0 | 0 | 0 | 0 | 0 |
| 1 | Ionic Bonding | 2 | 1 | 1 | 1 | 3 |
| 2 | Ionic Bonding | 2 | 1 | 1 | 1 | 2 |
| 3 | Covalent Bonding | 0 | 0 | ½ | 0 | ½ |
| 4 | Entrapment | 0 | 0 | 0 | 0 | ½ |
| 5 | Entrapment | 0 | 0 | 0 | 0 | 0 |
| 6 | Ionic Bonding | 3 | 2 | 1 | 3 | 3 |
| 7 | Entrapment | 1 | 1 | 0 | 1 | 1 |
| 8 | Ionic Bonding | ½ | 0 | 3 | 0 | 1 |
| 9 | Ionic Bonding | ½ | 0 | 2 | 0 | 1½ |
| 10 | Covalent Bonding | 1 | 1 | 0 | 1 | 2 |
| 11 | Covalent Bonding | 2 | 1 | 1 | 2 | 2 |
| 12 | Covalent Bonding | 2 | 1 | ½ | 1 | 3 |
| 13 | Covalent Bonding | 2 | 3 | 1 | 1½ | 1 |
| 14 | Covalent Bonding | 1 | ½ | 3 | 1 | 3 |
| 15 | Covalent Bonding | 1 | 2 | 1 | 2 | 3 |
| 16 | Covalent Bonding | ½ | 2 | 0 | 0 | 1 |

Analysis

Upon review of the results for the inhibitory activity of the coated polydimethylsiloxane substrates produced in the Control Example and Examples 1–16 against bacterial/microbial growth as shown in Table 2, many trends can be seen. The Control Example (i.e., without active ingredient coatings) showed a negative response in antimicrobial testing. Among the seven antimicrobials tested, chlorhexidine demonstrated high activity, both in the ability to suppress the colonization and its spectrum of action. Moreover, the mode of linkage contributes significantly to the results of the bioassay. For instance, ionic interaction can offer higher concentrations of the active component in the incubation media. Meanwhile, immobilization by entrapping the antimicrobial(s) in the bulk polymer coating is expected to show a more durable time of action, but it is preferred that the concentration of the active ingredient be reduced (compare the results of Examples 6 and 7). The combined use of chlorhexidine and 3,5-dimethyl-4-chlorophenol through covalent bonding (see Examples 10–13) is quite advantageous as it has the positive merit of improved activity versus *Pseudomonas* species. In doing so, the ratio of chlorhexidine and 3,5-dimethyl-4-chlorophenol can be well optimized. As is evident from a comparison with Examples 10–13, the concentration ratio is critical for the best performance.

Therefore, it can be seen that this work has provided an improved antimicrobial polymeric composition that may be easily applied as a coating to a substrate to provide an article which has excellent antimicrobial properties. The antimicrobial polymeric composition has several coating applications including, without limitation, medical devices.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A polymeric composition having antimicrobial properties, the polymeric composition comprising: a crosslinked chemical combination of (i) a polymer having side chains along a backbone forming the polymer, at least two of the side chains containing an amino group, (ii) an antimicrobial agent selected from the group consisting of quaternary ammonium compounds, gentian violet compounds, substituted or unsubstituted phenols, biguanide compounds, iodine compounds, and mixtures thereof, and (iii) a crosslinking agent containing at least two functional groups capable of reacting with the amino groups; wherein the polymer is a polyamide, and the polymer is synthesized by (i) reacting a monomer selected from the group consisting of unsaturated carboxylic acids, esters of unsaturated carboxylic acids, anhydrides of unsaturated carboxylic acids, and mixtures thereof, and a first amine to form an intermediate reaction product, wherein the first amine is selected from the group consisting of $RNH_2$, $RR_1NH$, polyalkylene polyamines, and mixtures thereof, and (ii) reacting the intermediate reaction product and a second amine to form the polyamide, wherein the second amine is selected from the group consisting of $R_2NH_2$, $R_2R_3NH$, polyalkylene polyamines, and mixtures thereof, wherein R, $R_1$, $R_2$ and $R_3$ can be the same or different and each contain between about 1 and 50 carbon atoms and are optionally substituted with heteroatoms oxygen, nitrogen, sulfur, and phosphorus or combinations thereof: and at least one of the selected amines includes at least two amino groups.

2. The polymeric composition of claim 1 wherein R and $R_1$ are alkyl.

3. The composition of claim 2 wherein the second amine is a polyalkylene polyamine.

4. The composition of claim 3, wherein the first amine comprises tetradecylamine and the polyalkylene polyamine comprises pentaethylenehexamine.

5. The composition of claim 1, wherein the monomer is selected from the group consisting of unsaturated dicarboxylic acids, esters of unsaturated dicarboxylic acids, anhydrides of unsaturated dicarboxylic acids, and mixtures thereof.

6. The composition of claim 5, wherein the monomer is selected from the group consisting of maleic anhydride, maleic acid esters, and mixtures thereof.

7. The polymeric composition of claim 1, wherein the antimicrobial agent is selected from the group consisting of cetyl pyridinium chloride, gentian violet, dimethyl gentian violet, dimethylchlorophenol, triclosan, thymol, chlorhexidine, iodine, and mixtures thereof.

8. The composition of claim 1 wherein the crosslinking agent is selected from the group consisting of phosphines having the general formula $(A)_3P$, wherein A is hydroxyalkyl, and mixtures thereof.

9. The composition of claim 8, wherein the crosslinking agent comprises tris(hydroxymethyl)phosphine.

10. The composition of claim 1 wherein the antimicrobial agent comprises chlorhexidine and dimethylchlorophenol.

11. The composition of claim 1 wherein the antimicrobial agent comprises dimethylchlorophenol.

12. The composition of claim 1, wherein the antimicrobial agent comprises triclosan.

13. The composition of claim 1 wherein the antimicrobial agent comprises thymol.

14. The composition of claim 1 wherein the antimicrobial agent comprises cetyl pyridinium chloride.

15. The composition of claim 1 wherein the antimicrobial agent comprises gentian violet, dimethyl gentian violet, or a mixture thereof.

16. The composition of claim 1 wherein the antimicrobial agent comprises chlorhexidine.

17. The composition of claim 1 wherein the antimicrobial agent comprises iodine, an iodine complex, or a mixture thereof.

18. A process for rendering the surface of a substrate antimicrobial, the process comprising:
(a) providing a polymer having side chains along a backbone forming the polymer, at least two of the side chains containing an amino group; wherein the polymer is a polyamide, and the polyamide is synthesized by:
  (i) reacting a monomer selected from the group consisting of unsaturated carboxylic acids, esters of unsaturated carboxylic acids, anhydrides of unsaturated carboxylic acids, and mixtures thereof, and a first amine to form an intermediate reaction product, wherein the first amine is selected from the group consisting of $RNH_2$, $RR_1NH$, polyalkylene polyamines and mixtures thereof, and
  (ii) reacting the intermediate reaction product and a second amine to form the polyamide, wherein the second amine is selected from the group consisting of $R_2NH_2$, $R_2R_3NH$, polyalkylene polyamines and mixtures thereof, wherein R, $R_1$, $R_2$ and $R_3$ can be the same or different and each contain between about 1 and 50 carbon atoms and are optionally substituted with heteroatoms oxygen, nitrogen, sulfur, and phosphorus or combinations thereof; and at least one of the selected amines includes at least two amino groups;
(b) mixing the polymer with a crosslinking agent and an antimicrobial agent selected from the group consisting of quaternary ammonium compounds, gentian violet compounds, substituted or unsubstituted phenols, biguanide compounds, iodine compounds, and mixtures thereof, to produce a polymer solution, the crosslinking agent containing at least two crosslinking functional groups capable of reacting with the amino groups; and
(c) coating at least a portion of the substrate with the polymer solution to produce a crosslinked polymer coating on the substrate.

19. The process of claim 18 wherein the crosslinking agent selected from the group consisting of polyaldehydes, phosphines having the general formula $(A)_3P$, wherein A is hydroxyalkyl, and mixtures thereof.

20. The process of claim 18 wherein the crosslinking agent is selected from the group consisting of phosphines having the general formula $(A)_3P$, wherein A is hydroxyalkyl, and mixtures thereof.

21. The process of claim 18 wherein the substrate comprises a polymeric material selected from the group consisting of polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof.

22. The process of claim 18 wherein the antimicrobial agent is selected from the group consisting of cetyl pyridinium chloride, gentian violet, dimethyl gentian violet, dimethylchlorophenol, triclosan, thymol, chlorhexidine, iodine, and mixtures thereof.

23. The process of claim 18 wherein R and $R_1$ are alkyl.

24. The process of claim 23 wherein the second amine is a polyalkylene polyamine.

25. The process of claim 18, wherein the monomer is selected from the group consisting of maleic anhydride, maleic acid esters, and mixtures thereof.

26. The process of claim 24, wherein the first amine comprises tetradecylamine and the polyalkylene polyamine comprises pentaethylenehexamine.

27. A polyamide material formed from:
(A) a polyamide formed from a mixture which comprises:
  one or more monomers selected from the group consisting of unsaturated carboxylic acids, esters of unsaturated carboxylic acids, anhydrides of unsaturated carboxylic acids, and mixtures thereof, and one or more amines selected from the group consisting of polyalkylene polyamines and amines having the formula RNH$_2$ or RR$_1$NH, wherein R and R$_1$ contain between 1 and 50 carbon atoms and are optionally substituted with heteroatoms oxygen, nitrogen, sulfer, phosphorus, and combinations thereof, and wherein at least one of the selected amines includes at least two amino groups; and (B) an antimicrobial agent comprising an agent selected from the group consisting of quaternary ammonium compounds, gentian violet compounds, substituted or unsubstituted phenols, biguanide compounds, iodine compounds, and mixtures thereof;

(C) a crosslinking agent containing at least two functional groups capable of reacting with amino groups.

28. The polyamide material of claim 27, wherein the crosslinking agent comprises a phosphine having the general formula (A)$_3$P, wherein A is hydroxyalkyl.

29. The polyamide material of claim 28, wherein the crosslinking agent comprises tris(hydroxymethyl) phosphine.

30. A The polyamide material of claim 27, wherein the crosslinking agent comprises gluteraldehyde and tris(hydroxymethyl)phosphine.

31. The polyamide material of claim 27, wherein the crosslinking agent comprises an agent selected from the group consisting of aliphatic isocyanate compounds having 2 or more —N=C=O groups; aromatic isocyanate compounds having 2 or more —N=C=O groups; aromatic aldehyde compounds having 2 or more —CHO groups; phosphines having the general formula (A)$_2$P(B) wherein A is hydroxyalkyl, and B is hydroxyalkyl, alkyl, or aryl; epoxy resins having end groups of the formula:

and mixtures thereof.

32. The polyamide material of claim 27, wherein the antimicrobial agent comprises an agent selected from the group consisting of cetyl pyridinium chloride, gentian violet, dimethyl gentian violet, dimethylchlorophenol, triclosan, thymol, chlorhexidine, iodine, and mixtures thereof.

33. The polyamide material of claim 27, wherein the one or more monomers are selected from the group consisting of maleic anhydride, maleic acid esters, and mixtures thereof.

34. The polyamide material of claim 27, wherein the one or more monomers are selected from the group consisting of unsaturated dicarboxylic acids, esters of unsaturated dicarboxylic acids, and anhydrides of unsaturated dicarboxylic acids and mixtures thereof.

35. The polyamide material of claim 27, wherein the one or more amines comprise tetradecylamine.

36. The polyamide material of claim 27, wherein the one or more amines comprise pentaethylenehexamine.

37. The polyamide material of claim 27, wherein the one or more amines comprise polyalkylene polyamine and an amine having the formula RNH$_2$, wherein R is alkyl.

38. The polymeric composition of claim 1 wherein the crosslinking agent is selected from the group consisting of aliphatic isocyanate compounds having 2 or more —N=C=O groups; aromatic isocyanate compounds having 2 or more —N=C=O groups; aromatic aldehyde compounds having 2 or more —CHO groups; phosphines having the general formula (A)$_2$P(B) wherein A is hydroxyalkyl, and B is hydroxyalkyl, alkyl, or aryl; epoxy resins having end groups of the formula:

and mixtures thereof.

39. The polymeric composition of claim 1, wherein the crosslinking agent comprises gluteraldehyde and tris(hydroxymethyl)phosphine.

40. The process of claim 18, wherein the crosslinking agent is selected from the group consisting of aliphatic isocyanate compounds having 2 or more —N=C=O groups; aromatic isocyanate compounds having 2 or more —N=C=O groups; aromatic aldehyde compounds having 2 or more —CHO groups; phosphines having the general formula (A)$_2$P(B) wherein A is hydroxyalkyl, and B is hydroxyalkyl, alkyl, or aryl; epoxy resins having end groups of the formula:

and mixtures thereof.

41. The process of claim 18, wherein the monomer is selected from the group consisting of unsaturated dicarboxylic acids, esters of unsaturated dicarboxylic acids, anhydrides of unsaturated dicarboxylic acids, and mixtures thereof.

42. The process of claim 18, wherein the monomer is selected from the group consisting of maleic anhydride, maleic acid esters, and mixtures thereof.

43. The process of claim 18, wherein the crosslinking agent comprises gluteraldehyde and tris(hydroxymethyl) phosphine.

44. A polymeric material comprising:

(A) a polymer formed by a process comprising:
reacting a reaction mixture comprising a monomer selected from the group consisting of unsaturated carboxylic acids, esters of unsaturated carboxylic acids, anhydrides of unsaturated carboxylic acids, and mixtures thereof; and one or more amines selected from polyalkylene polyamines and amines having the formula RNH$_2$ or RR$_1$NH, wherein R and R$_1$ contain between 1 and 50 carbon atoms and are optionally substituted with heteroatoms oxygen, nitrogen, sulfur, phosphorus, and combinations thereof, wherein the selected amine includes at least one amine having at least two amino groups; and (B) an antimicrobial agent comprising an agent selected from the group consisting of quaternary ammonium compounds, gentian violet compounds, substituted or unsubstituted phenols, biguanide compounds, iodine compounds, and mixtures thereof.

45. The polymeric material of claim 44, wherein the monomer is selected from the group consisting of unsaturated dicarboxylic acids, esters of unsaturated dicarboxylic acids, anhydrides of unsaturated dicarboxylic acids, and mixtures thereof.

46. The polymeric material of claim 45, wherein the monomer is selected from the group consisting of maleic anhydride, maleic acid esters, and mixtures thereof.

47. The polymeric material of claim 46, wherein the antimicrobial agent is selected from the group consisting of cetyl pyridinium chloride, gentian violet, dimethyl gentian violet, dimethylchlorophenol, triclosan, thymol, chlorhexidine, iodine, and mixtures thereof.

48. The polymeric material of claim 44, wherein R and $R_1$ are alkyl.

49. The polymeric material of claim 44, wherein one or more selected amines comprises a polyalkylene polyamine.

50. The polymeric material of claim 44, wherein $RNH_2$ comprises tetradecylamine and the polyalkylene polyamine comprises pentaethylenehexamine.

51. The polyamide material of claim 44, wherein the one or more amines comprise polyalkylene polyamine and an amine having the formula $RNH_2$, wherein R is alkyl.

* * * * *

UNITED STATES PATENT AND TRADEMARK OFFICE
CERTIFICATE OF CORRECTION

PATENT NO. : 6,939,554 B2
DATED : September 6, 2005
INVENTOR(S) : William F. McDonald, Zhi-Heng Huang and Stacy C. Wright It is certified that error appears in the above-identified patent and that said Letters Patent is hereby corrected as shown below:

Column 22,
Line 32, between "agent" and "selected" please insert -- is --.

Signed and Sealed this

Thirteenth Day of December, 2005

JON W. DUDAS
*Director of the United States Patent and Trademark Office*